United States Patent [19]

Stusack et al.

[11] Patent Number: 4,640,167

[45] Date of Patent: Feb. 3, 1987

[54] TAPE DISPENSER

[75] Inventors: Hans Stusack; Peter Schulz, both of Tettnang, Fed. Rep. of Germany

[73] Assignee: Franz Sachs & Co. KG, Fed. Rep. of Germany

[21] Appl. No.: 741,539

[22] Filed: Jun. 5, 1985

[30] Foreign Application Priority Data

Jun. 5, 1984 [DE] Fed. Rep. of Germany ....... 3420873

[51] Int. Cl.$^4$ .............................................. B26D 5/10
[52] U.S. Cl. ........................................ 83/649; 83/436; 83/444; 83/611; 225/15; 225/16; 225/54
[58] Field of Search ................. 83/649, 436, 444, 611; 225/15, 16, 54

[56] References Cited

U.S. PATENT DOCUMENTS

| 1,726,883 | 9/1929 | Brooks | 83/649 X |
| 2,792,885 | 5/1957 | Greene | 83/649 X |
| 3,037,477 | 6/1962 | Krueger et al. | 83/649 X |
| 3,117,478 | 1/1964 | Deming | 83/202 |
| 3,306,806 | 2/1967 | Seropian | 83/649 X |
| 3,470,781 | 10/1969 | Domeny | 83/436 |
| 3,971,280 | 7/1976 | Inka | 83/649 X |

Primary Examiner—Donald R. Schran
Attorney, Agent, or Firm—McGlew and Tuttle

[57] ABSTRACT

A device for dispensing tape in desired lengths from a supply reel which is rotatably supported in a housing and fed out by means of a manually actuable drive wheel which also has, in the housing, a knife which is manually actuable in the direction of the tape to cut the tape. The device makes it easy to single-handedly separate from the supply reel a desired length of tape.

10 Claims, 1 Drawing Figure

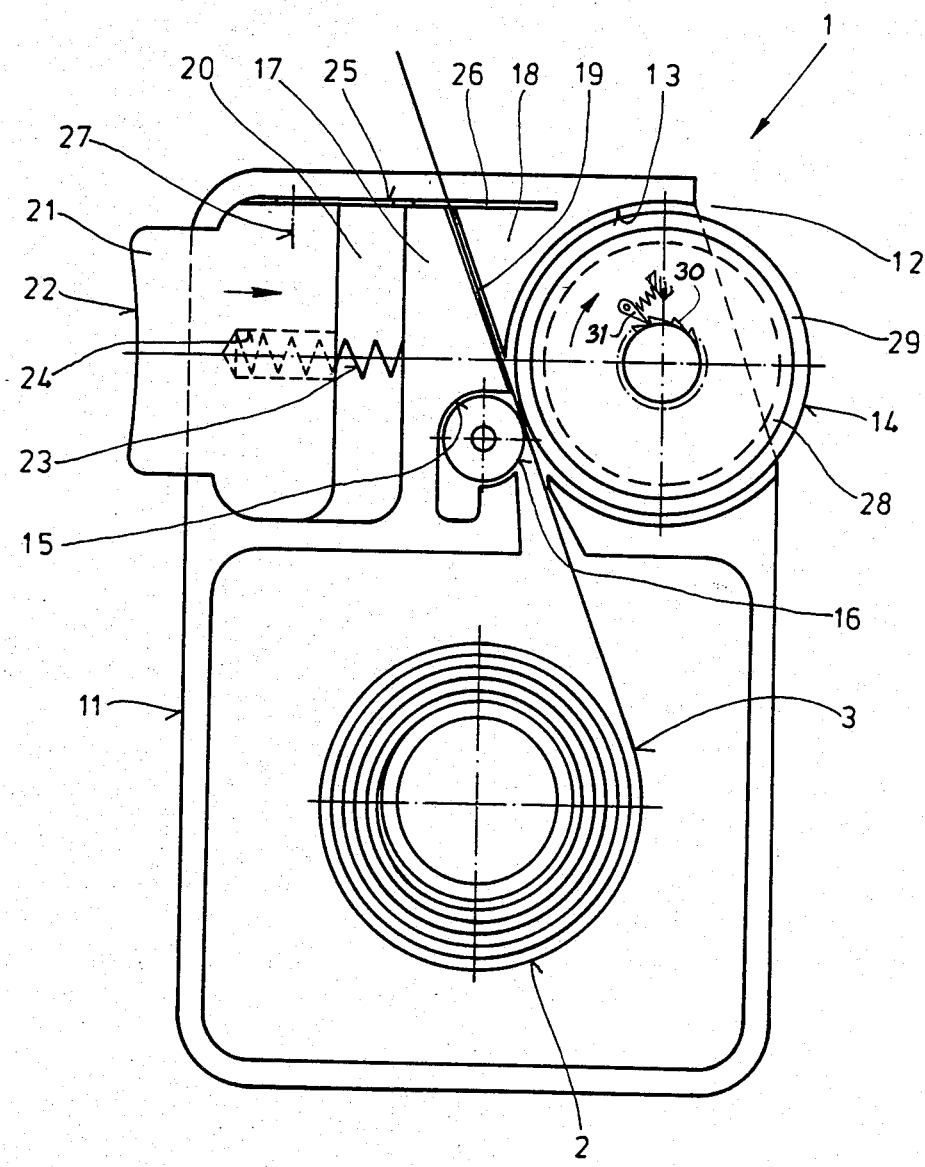

TAPE DISPENSER

FIELD AND BACKGROUND OF THE INVENTION

The present invention relates in general to tape dispensers and in particular to a new and useful device for dispensing tape, thread, foil strips or any other elongated material.

Dispensers of this kind are known in a variety of designs and have proved useful in practice. However, to separate a length of the tape is frequently very difficult since the tape protruding from the housing must be pulled by one hand over a knife which is fixed to the housing, while at the same time, the housing must be firmly held in place by the other hand. Further, in spite of this complicated handling, it frequently happens that tapes; particularly foil strips resistant to tearing, cannot be cut smoothly so that additional cutters are needed to separate a definite length in a short time and smoothly. A dentist applying such tape lengths is therefore dependent on a third person for cutting the tape.

SUMMARY OF THE INVENTION

The present invention is directed to a device of the above mentioned kind permitting to easily cut desired lengths from a supply reel. Primarily, it must be ensured that both the adjustment of the desired length and the cutting can be effected single-handedly and simply without problems even under difficult conditions. Further, the costs of manufacture must be kept low and the operation must remain reliable.

Accordingly, an object of the present invention is to provide a device for dispensing elongated materials held on a supply reel of the material, comprising a housing defining a space for rotatably receiving a supply reel of the material to be dispensed, a manually rotatable drive wheel rotatably mounted to the housing having an outer periphery with at least a portion of the outer periphery accessible from outside the housing, guide means in said housing for extablishing a guide path for elongaged material from the supply reel, said drive wheel extending tangentially to said guide path for engagement with elongated material from the supply reel to move the material along the guide path with rotation of the drive wheel, and a cutting knife movably mounted in said housing across said guide path for cutting the elongated material at a marginal zone of the housing, the knife being manually engageable from outside the housing for moving the knife to cut the elongated material.

A still further object of the invention is to provide such a device wherein a backup roller is rotatably mounted in the housing on a side of the guide path opposite from and adjacent to the drive wheel for cooperating with the drive wheel to move the elongated material along the guide path. The drive wheel and/or the backup roller may be mounted within a partially circular space within the housing having a shape which at least partly corresponds to the outer circumference of the drive wheel and/or the backup roller. Either the drive wheel or the backup roller or both may be provided with an outer circumferential coating of high coefficient of friction material such as rubber. The drive wheel may be provided with a circumferential groove which receives a rubber ring to provide the high coefficient of friction material.

A still further object of the invention is to form the guide means of a slot which extends obliquely to longitudinal axis of the housing within the housing and which is defined between intermediate spaced apart walls. A further guide slot may be provided for the cutting knife which extends across the guide path and which preferably has a cutting edge which is inclined with respect to the direction of movement of the knife. This facilitates easy cutting of the elongated material.

A pushbutton may be mounted for movement in the housing and be accessible from outside of the housing, the cutting knife being fixed to the pushbutton to effect movement of the cutting knife. A compression spring may be provided between the pushbutton and the housing for biasing the pushbutton in a direction out of the housing and for biasing the cutting knife in a direction away from the guide path.

To prevent the drive wheel from turning in a backwards direction and thus for moving the elongated material back into the housing rather than out of the housing, the drive wheel is equipped with a ratchet and pawl lock.

The inventive device is both simple in construction and inexpensive in manufacture and also very simple to operate and makes it possible to separate any desired length from the supply reel with a single hand and without problems. Upon advancing the tape by means of a hand operated drive wheel through a guideway provided in the housing, the knife can be actuated with a finger of the hand in which the housing is held while the drive wheel may be rotated by the thumb of the same hand. The tape is thus fed out of the housing, and can be cut at any desired location. No difficulties arise. Rather a simple and reliable operation is always ensured, so that a great variety of applications can be found.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE in the application is a longitudinal sectional view of the inventive device.

DESCRIPTION OF THE PREFERRED EMBODIMENT

Referring to the drawing in particular, the invention embodied therein comprises a dispensing device for dispensing an elongated material such as tape, thread or foil.

The device generally designated 1 substantially comprises a supply reel 2 wherefrom a desired length of a tape 3 can be unwound and which is mounted for rotation in a housing 11, a drive wheel 14 operating on tape 3, and a cutting knife 25 by which the tape can be cut in a marginal zone of the housing. Drive wheel 14 and knife 25 are actuable with the fingers of a single hand holding the housing 11.

The tape 3 is passed through and guided in a slot 19 which is formed by two spaced apart intermediate walls 17, 18 of housing 11 and can be moved, i.e. displaced through the slot, by means of drive wheel 14 in the direction of the arrow. A backup roller 16 is provided at the tape side remote from drive wheel 14, as an abutment, so that the tape is firmly squeezed and its advance is ensured. Both drive wheel 14 and backup roller 16 are mounted for rotation in respective circular segment recesses 13, 15 of the housing which is preferably made in two parts of plastic. No further guide elements are necessary. Housing 11 is cut open in one of its corners 12, so that drive wheel 14 is easy to actuate.

Cutting knife 25 operating on the tape is formed by a blade which is guided in a slot 26 parallel to the upper edge of housing 11, and which has its cutting edge inclined in the axial direction. The blade is secured to a pushbutton 21 by a rivet or pin, as indicated in broken lines at 26. Pushbutton 21 has an actuating surface 22 and, in the shown example, is displaceably received in a recess 20 at the housing side remote from drive wheel 14, and can be pressed down against the action of a compression spring 23 which is guided in a bore 24. This ensures an automatic return of pushbutton 21 into its initial position.

To cut away a definite length of tape 3, it suffices to rotate drive wheel 14 until the desired length protrudes from housing 11. Then, pushbutton 21 is actuated until knife 25 cuts the tape and the separated length can be removed. Since drive wheel 14 is provided with a plurality of juxtaposed rubber rings 29 received in circumferential grooves 28, the tape is satisfactorily held fast for cutting, and this hold may even be improved by applying a slight additional force on the drive wheel.

A ratchet 30 is fixed for rotation with wheel 14 and is locked by pawl 31 against rotation opposite to the arrow.

While a specific embodiment of the invention has been shown and described in detail to illustrate the application of the principles of the invention, it will be understood that the invention may be embodied otherwise without departing from such principles.

What is claimed is:

1. A device for dispensing elongated material which is stored on a supply reel, comprising a housing having outer walls and defining an inerior supply reel space for rotatably receiving a supply reel of elongated material, guide means in said housing defining a guide path from said supply reel space through one of said outer walls for elongated material to leave said housing, a manually rotatable drive wheel rotatably mounted at one end of said one outer wall and in said housing, said drive wheel having an outer periphery, a part of said outer periphery of said drive wheel being accessible from outside said outer walls of said housing and said outer periphery tangentially intersecting said guide path for engaging elongated material so that rotation of said drive wheel in one direction moves elongated material along said guide path from said supply reel space out of said housing, a cutting knife movably mounted in said housing in a direction across said guide path and parallel to said one outer wall and adjacent said one outer wall of said housing for cutting elongated material supplied from said supply reel space along said guide path by said drive wheel, said housing including a displacement slot extending parallel to said one outer wall of said housing which is adjacent to said cutting knife, said cutting knife being displaceable able in said slot, said slot extending across said guide path, a pushbutton movably mounted in said housing in a direction parallel to said one outer wall and toward said drive wheel, said pushbutton being fixed to said cutting knife and having a portion accessible from outside said housing on an opposite side of said one outer wall from said drive wheel, and a spring engaged between said pushbutton and said housing for biasing said pushbutton in a direction out of said housing, and away from said drive wheel for moving said knife in a direction away from said guide path.

2. A device according to claim 1, wherein said housing is substantially rectangular, said housing having a first corner with a cutout portion through which said drive wheel is rotatable for accessing an outer periphery of said drive wheel from an exterior of said housing, said housing having an opposite corner on a same side of said housing as said drive wheel, said pushbutton being movable out of said housing adjacent to said opposite corner, said one outer wall being between said first mentioned and opposite corners, said guide path extending through said one outer wall, said supply reel space being rectangular and being disposed on the side of said housing opposite from said first mentioned and opposite corners.

3. A device according to claim 2, wherein said drive wheel has a circular groove in an outer periphery thereof, and a rubber ring in said groove for improving frictional engagement between elongated material to be dispensed and said drive wheel.

4. A device according to claim 2, including a backup roller rotatably mounted in said housing on a side of said guide path opposite from said drive wheel and adjacent said drive wheel for cooperating with said drive wheel to move elongated material along said guide path between said guide wheel and said roller.

5. A device according to claim 4, wherein said housing includes a first circular segment shaped recess for receiving said drive wheel and a second circular segment shaped recess for receiving said roller, said recesses being positioned on opposite sides of said guide path.

6. A device according to claim 4, wherein at least one of said drive wheel and backup roller have outer peripheries coated by a high coefficient of friction material.

7. A device according to claim 6, wherein said high coefficient of friction material comprises a rubber ring, at least one of said drive wheel and roller having a circumferential groove, said rubber ring disposed in said circumferential groove.

8. A device according to claim 2, wherein said housing has side walls extending in a longitudinal direction, said guide path extending obliquely to said longitudinal direction, said guide means comprising a pair of spaced apart intermediate walls in said housing defining said guide path therebetween.

9. A device according to claim 2, wherein said cutting knife has an edge which extends at an incline with respect to a direction of movement of said cutting knife.

10. A device according to claim 2, including ratchet and pawl means connected to said drive wheel for permitting rotation of said drive wheel only in a direction for dispensing elongated material from said housing and not in an opposite direction.

* * * * *